United States Patent
Noonan et al.

(10) Patent No.: US 11,141,222 B2
(45) Date of Patent: Oct. 12, 2021

(54) UNIVERSAL FIBER-OPTICAL REALSHAPE INSERT

(71) Applicant: KONINKLIJKE PHILIPS N.V., Eindhoven (NL)

(72) Inventors: David Paul Noonan, New York, NY (US); Molly Lara Flexman, Melrose, MA (US); Dirk Dijkkamp, Waalre (NL)

(73) Assignee: Koninklijke Philips N.V., Eindhoven (NL)

( * ) Notice: Subject to any disclaimer, the term of this patent is extended or adjusted under 35 U.S.C. 154(b) by 801 days.

(21) Appl. No.: 15/578,860

(22) PCT Filed: Jun. 9, 2016

(86) PCT No.: PCT/EP2016/063191
§ 371 (c)(1),
(2) Date: Dec. 1, 2017

(87) PCT Pub. No.: WO2016/198539
PCT Pub. Date: Dec. 15, 2016

(65) Prior Publication Data
US 2018/0153623 A1    Jun. 7, 2018

Related U.S. Application Data

(60) Provisional application No. 62/174,547, filed on Jun. 12, 2015.

(51) Int. Cl.
*A61B 34/20* (2016.01)
*A61B 17/84* (2006.01)
(Continued)

(52) U.S. Cl.
CPC .......... *A61B 34/20* (2016.02); *A61B 17/7074* (2013.01); *A61B 17/848* (2013.01);
(Continued)

(58) Field of Classification Search
CPC ... A61B 34/20; A61B 17/7074; A61B 17/848; A61B 17/56; A61B 90/60;
(Continued)

(56) References Cited

U.S. PATENT DOCUMENTS

| 2013/0188855 A1 | 7/2013 | Desjardins et al. |
| 2015/0359456 A1 | 12/2015 | Urban et al. |
| 2016/0223753 A1 | 8/2016 | Noonan et al. |

FOREIGN PATENT DOCUMENTS

| WO | 0133165 A1 | 5/2001 | |
| WO | WO-2015044814 A1 * | 4/2015 | ........... G02B 6/3624 |

OTHER PUBLICATIONS

Manbachi, A. et al., "Guided pedicle screw insertion: techniques and training," The Spine Journal, Article in Press (2013).
(Continued)

*Primary Examiner* — Peter Luong (57) ABSTRACT

A universal FORS insert (20-22) for a plurality of different surgical instruments with each surgical instrument (50) including a lumen (51). Universal FORS insert (20-22) employs a FORS sensor (30) for generating sensing data indicative of a reconstructed shape of a tracking segment (30T) of FORS sensor (30). Universal FORS insert (20-22) further employs a protective sleeve (40) permanent encircling a portion or an entirety of tracking segment (30T) for inserting tracking segment (30T) into and retracting FORS insert (20-22) from within the lumen (51) of each surgical instrument (50). The plurality of surgical instruments may be a same version or different versions of a same instrument type of surgical instrument (e.g., same sized k-wires and/or different sized k-wires), or different instrument types of surgical instruments (e.g., a j-needle and an awl).

15 Claims, 9 Drawing Sheets

(51) Int. Cl.
*A61B 90/90* (2016.01)
*A61B 17/70* (2006.01)
*A61B 17/00* (2006.01)
*A61B 17/56* (2006.01)
*A61B 5/00* (2006.01)
*A61B 5/1459* (2006.01)

(52) U.S. Cl.
CPC ............ *A61B 90/90* (2016.02); *A61B 5/0084* (2013.01); *A61B 5/1459* (2013.01); *A61B 17/56* (2013.01); *A61B 2017/00482* (2013.01); *A61B 2017/00725* (2013.01); *A61B 2034/2061* (2016.02)

(58) Field of Classification Search
CPC .......... A61B 2017/00482; A61B 2017/00725; A61B 2034/2061; A61B 5/0084; A61B 5/1459
See application file for complete search history.

(56) References Cited

OTHER PUBLICATIONS

Ozgur, B. et al., "Minimally Invasive Spine Surgery: A practical guide to anatomy and techniques," Springer (2009).
Winkelhagen, J., et al., "Preliminary results of cannulated screw fixation for isolated pubic ramus fractures," Strategies Trauma Limb Reconstr 7(2) 87-91 (2012).

* cited by examiner

UNIVERSAL FIBER-OPTICAL REALSHAPE INSERT

CROSS-REFERENCE TO PRIOR APPLICATIONS

This application is the U.S. National Phase application under 35 U.S.C. § 371 of International Application Serial No. PCT/EP2016/063191, filed on Jun. 9, 2016, which claims the benefit of U.S. application Ser. No. 62/174,547, filed on Jun. 12, 2015. This application is hereby incorporated by reference herein.

FIELD OF THE INVENTION

The present disclosure generally relates to tracking instruments during a surgical procedure. The present invention specifically relates to a novel and inventive universal Fiber-Optical RealShape™ ("FORS") insert for tracking the instruments during the surgical procedure, particularly for tracking orthopedic instruments (e.g., a Kirschner wire, a Jamshidi® needle, an awl, etc.) during an orthopedic procedure involving the musculoskeletal system (e.g., spinal fixation, pedicle screw placement, trauma surgery, oncology and neurosurgery).

BACKGROUND OF THE INVENTION

One orthopedic instrument known in the art is a Kirschner wire ("k-wire") as a guide, anchor, or for stabilizing bone fragments. More particularly, a k-wire is a metal wire having a small diameter (e.g., 1-5 mm) and is drilled into bone on a temporary or permanent basis. A k-wire may be utilized alone or with cannulated screws for stabilizing fractures or for fixation of the spine. K-wires are also used in the fixation of fractures and in trauma surgery.

Another orthopedic instrument known in the art is a Jamshidi® needle ("j-needle"), which is a cylindrical needle having a tapered cutting tip insertable within a lumen of the needle. A key feature of the j-needle is the flat handle surface that can be used with a mallet to tap and insert the needle into bone. After insertion into the bone and upon removal of the cutting tip from within the lumen, a k-wire or other tool is inserted within the lumen of the needle.

An exemplary pedicle screw placement as known in the art generally consists of:
  (1) positioning a patient prone on a table;
  (2) positioning a C-arm to acquire a good view of the patient's pedicle;
  (3) creating access to the patient's spine;
  (4) docking a j-needle on the junction between the transverse process and the facet complex;
  (5) gently tapping the j-needle with a mallet to advance the j-needle through the pedicle, either freehand or under fluoroscopic visualization;
  (6) upon the j-needle reaching one quarter or half the depth of the vertebral body, removing the cutting tip from the lumen of the j-needle and inserting a k-wire into the lumen of the j-needle;
  (7) passing the k-wire further into the bone and removing the j-needle;
  (8) placing cannulated muscle dilators over the k-wire; and
  (9) tapping the pedicle and placing the appropriate cannulated screw.

In the above spinal fusion, it is important to accurately place screws within the pedicle in order to fuse two or more vertebrae of the spine, particularly due to the close proximity of vital nerves and vessels. For freehand placement of a pedicle screw as described above, there are high rates of misplacement and critical breaches. Image-guided surgery for orthopedics is therefore preferred.

Specifically, imaging is used in spinal surgery for both pre-operative planning and assessment and for intra-operative guidance (e.g., CT, MRI, Fluoroscopy, X-ray, etc.). Intraoperative fluoroscopy is commonly used to verify the positioning of the j-needle and/or k-wire before the drill or screw is placed in position. The drawback of fluoroscopy is that it imparts ionizing radiation to both the patient and the doctor, and it provides a two-dimensional ("2D") projection of a three-dimensional ("3D") position.

To address this drawback, computer assisted image-guided surgery involves the addition of a navigation tools to pre-operative and/or intra-operative imaging in order to provide 3D guidance of orthopedic instruments with respect to the anatomy during the procedure. Optical trackers are the most common form of such navigation tools and are required to be attached to the working orthopedic instrument. One drawback with optical trackers is the optical trackers must always remain in the camera line-of-sight. In addition, the optical trackers are quite large and thus must be attached at the proximal end of any orthopedic instrument. This limits an ability of optical trackers to track small and flexible orthopedic instruments which lack the sufficient stiffness to infer tip position from a proximally attached optical tracker (e.g., a k-wire).

Alternatively, electromagnetic tracking has been used with coils that are small enough to embed in the flexible and small orthopedic instruments. However, the accuracy of electromagnetic tracking may be impacted by metal objects in the field, which is a common issue in orthopedic procedures. In addition, an electromagnetic field generator is required, which may limit the workspace of the tracked orthopedic instruments.

SUMMARY OF THE INVENTION

The present disclosure provides a universal Fiber-Optical RealShape ("FORS") insert incorporating a FORS sensor that is (1) insertable into a lumen of a surgical instrument for tracking the surgical instrument during a surgical procedure, and (2) retractable from within the lumen of the surgical instrument for insertion into a lumen of another surgical instrument for tracking that surgical instrument during the same or a different surgical procedure. Additionally, the universal FORS sensor may serve as a surgical instrument.

For purposes of the inventions of the present disclosure, the terms "surgical instrument" and "surgical procedure" are to be interpreted as understood in the art of the present disclosure and as exemplary described herein.

Examples of general categories of a surgical procedure include, but are not limited to, cardiovascular, gynecology, abdominal, neurosurgery, obstetrics, ophthalmology, orthopedic, otolaryngology, reconstructive, thoracic, and urology. More particularly, examples of orthopedic procedures include, but are not limited to, spinal surgery, join/knee/hip/shoulder/ankle replacements, rotary cuff repair, ACL reconstruction, and arthroscopic surgery.

Examples of a surgical instrument in the form of surgical tools include, but are not limited to, scalpels, cauterizers, ablation devices, needles, forceps, k-wires and associated drivers, endoscopes, awls, screwdrivers, osteotomes, chisels, mallets, curettes, clamps, forceps, periosteomes and j-needles.

Examples of surgical instruments in the form of implantable implements include, but are not limited to, needles, pins, nails, screws, and plates.

For purposes of inventions of the present disclosure, the term "lumen" broadly encompasses a channel, cavity, duct, etc. that is (1) constructed within a surgical instrument as known in the art (e.g., lumen of a k-wire and lumen of a j-needle) or (2) constructed within a universal insert receiver adjoined to a surgical instrument with the term "universal insert receiver" broadly encompassing any mechanism (e.g., a connector, a clip, a clamp, a plug, etc.) adjoinable to a surgical instrument and having a lumen for receiving a universal FORS insert of the present disclosure in a manner that facilitates a tracking of the surgical instrument by the FORS sensor, and the term "adjoin" in any tense thereof broadly encompassing any type of permanent or detachable coupling, connecting, affixing, mounting, etc. of components involving direct physical contact between the components or an adjacent placement of the components.

For purposes of the inventions of the present disclosure, the term "Fiber-Optical RealShape ("FORS") sensor" broadly encompasses an optical fiber structurally configured as known in the art for extracting high density strain measurements of the optical fiber derived from light emitted into and propagated through the optical fiber and reflected back within the optical fiber in an opposite direction of the propagated light and/or transmitted from the optical fiber in a direction of the propagated light.

An example of a FORS sensor includes, but is not limited to, an optical fiber structurally configured under the principle of Optical Frequency Domain Reflectometry (OFDR) for extracting high density strain measurements of the optical fiber derived from light emitted into and propagated through the optical fiber and reflected back within the optical fiber in an opposite direction of the propagated light and/or transmitted from the optical fiber in a direction of the propagated light via controlled grating patterns within the optical fiber (e.g., Fiber Bragg Gratings), a characteristic backscatter of the optical fiber (e.g., Rayleigh backscatter) or any other arrangement of reflective element(s) and/or transmissive element(s) embedded, etched, imprinted, or otherwise formed in the optical fiber.

Commercially and academically, Fiber-Optical RealShape may also be known as optical shape sensing ("OSS").

One form of the inventions of the present disclosure is a universal FORS insert for a plurality of surgical instruments with the universal FORS insert employing a FORS sensor for generating sensing data indicative of a reconstructed shape of a tracking segment of the FORS sensor.

For purposes of the inventions of the present disclosure, the terms "sensing data", "shape" and "reconstruct" and any word tenses thereof are to be interpreted as understood in the art of the present disclosure and as exemplary described herein.

For purposes of the inventions of the present disclosure, the term "tracking segment" broadly encompasses a segment of the FORS sensor extending between the launch point and a distal end of the universal FORS insert, and a term "proximal segment" broadly encompasses a segment of the FORS sensor extending between the proximal end of the FORS sensor and the launch point.

For purposes of the inventions of the present disclosure, the terms, "launch point", "proximal end" and "distal end" are to be interpreted as understood in the art of the present disclosure and as exemplary described herein.

The universal FORS insert further employs a protective sleeve permanently encircling a portion or an entirety of the tracking segment that is insertable into and retractable from within a lumen of each surgical instrument.

For purposes of the inventions of the present disclosure, the terms "encircle", "insertable" and "retractable" and any word tenses thereof are to be interpreted as understood in the art of the present disclosure and as exemplary described herein.

For purposes of the inventions of the present disclosure, the term "protective sleeve" broadly encompasses a tubular body of a flexible material composition having a specified hardness for impeding any structural damage to the FORS sensor, and the term "permanently encircling" and any word tenses thereof broadly encompasses a continual, enduring, binding encirclement of the FORS sensor by the protective sleeve that facilitates numerous uses of the universal FORS insert for a plurality of surgical instruments of the same and/or different instrument types during the course of a single or multiple surgical procedures. As such, a "protective sleeve" of the present disclosure excludes the disposable use of surgical instruments as known in the art for temporarily encircling an optic fiber for a single insertion within a patient during a surgical procedure. For the universal FORS insert, the plurality of surgical instruments may be a same version of a same instrument type of surgical instrument (e.g., same sized k-wires), or a different version of a same instrument type of surgical instrument (e.g., different sized k-wires), or different instrument types of surgical instruments (e.g., a j-needle and an awl).

A second form of the inventions of the present disclosure is a method of operating a controller during a surgical procedure incorporating the universal FORS insert. In operation, the controller controls a registration of the FORS sensor to an imaging modality. Prior to the registration or subsequent to the registration, the controller controls a calibration of the FORS sensor to a first surgical instrument (e.g., a j-needle) upon the tracking segment of the FORS sensor as permanently encircled by the protective sleeve is inserted into the lumen of the first surgical instrument. Subsequent to the registration and calibration, the controller controls a display of a tracking visualization of the surgical instrument within an image of the patient within an image of a patient generated by the imaging modality responsive to sensing data indicative of a reconstructed shape of the tracking segment.

In furtherance of the surgical procedure, the controller controls a calibration of the FORS sensor to a second surgical instrument (e.g., a k-wire) upon the tracking segment of the FORS sensor is retracted from within the lumen of the first orthopedic instrument and inserted into a lumen of the second surgical instrument. Subsequent to the second calibration, the controller controls a display of a tracking visualization of the second surgical instrument within the image of the patient responsive to sensing data indicative of the reconstructed shape of the tracking segment.

For purposes of the present disclosure, the term "controller" broadly encompasses all structural configurations of an application specific main board or an application specific integrated circuit housed within or linked to a workstation for controlling an application of various inventive principles of the present invention as subsequently described herein. The structural configuration of the controller may include, but is not limited to, processor(s), computer-usable/computer readable storage medium(s), an operating system, application module(s), peripheral device controller(s), slot (s) and port(s).

Examples of a "workstation" include, but are not limited to, an assembly of one or more computing devices, a display/monitor, and one or more input devices (e.g., a keyboard, joysticks and mouse) in the form of a client computer, a desktop or a tablet.

For purposes of the present disclosure, the term "application module" broadly encompasses a component of the workstation consisting of an electronic circuit and/or an executable program (e.g., executable software and/or firmware) for executing a specific application.

For purposes of the present disclosure, the terms "imaging modality" and "imaging data" are to be interpreted as understood in the art of the present disclosure and as exemplary described herein.

The foregoing forms and other forms of the present invention as well as various features and advantages of the present invention will become further apparent from the following detailed description of various embodiments of the present invention read in conjunction with the accompanying drawings. The detailed description and drawings are merely illustrative of the present invention rather than limiting, the scope of the present invention being defined by the appended claims and equivalents thereof.

DETAILED DESCRIPTION OF THE PREFERRED EMBODIMENTS

The inventions of the present disclosure are premised on a FORS sensor including a proximal segment and a tracking segment having a boundary defined by a launch point that serves as a reference for reconstructing a shape of the tracking segment of the FORS sensor. As known in the art, the reconstructed shape of the FORS sensor provides a position and an orientation of an actual shape of the tracking segment within a tracking coordinate system as known in the art.

The inventions of the present disclosure provides a protective sleeve permanently encircling a portion or an entirety of the FORS sensor to impede any damage to the FORS sensor. The tracking segment as permanently encircled by the protective sleeve is insertable into and retractable from within a lumen of a plurality of surgical instruments being a same version of a same instrument type of surgical instrument (e.g., same sized k-wires), or a different version of a same instrument type of surgical instrument (e.g., different sized k-wires), or different instrument types of surgical instruments (e.g., a j-needle and an awl).

To facilitate an understanding of the various inventions of the present disclosure, the following description of FIGS. 1A-5B teaches basic inventive principles of a FORS sensing of surgical instruments during a surgical procedure. From this description, those having ordinary skill in the art will appreciate how to apply the inventive principles of the present disclosure for making and using various universal FORS inserts of the present disclosure. Please note the components of the universal FORS inserts of the present disclosure as shown in FIGS. 1A-5B are not drawn to scale, but drawn to conceptually visualize the inventive principles of the present disclosure.

Figure 1A:
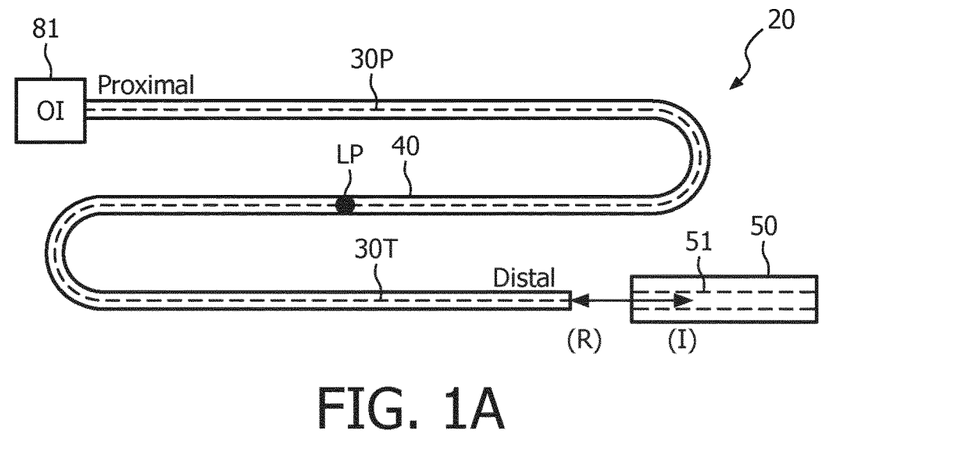
FIGS. 1A-1C illustrates exemplary embodiments of a universal FORS insert in accordance with the inventive principles of the present disclosure.
Figure 1B:
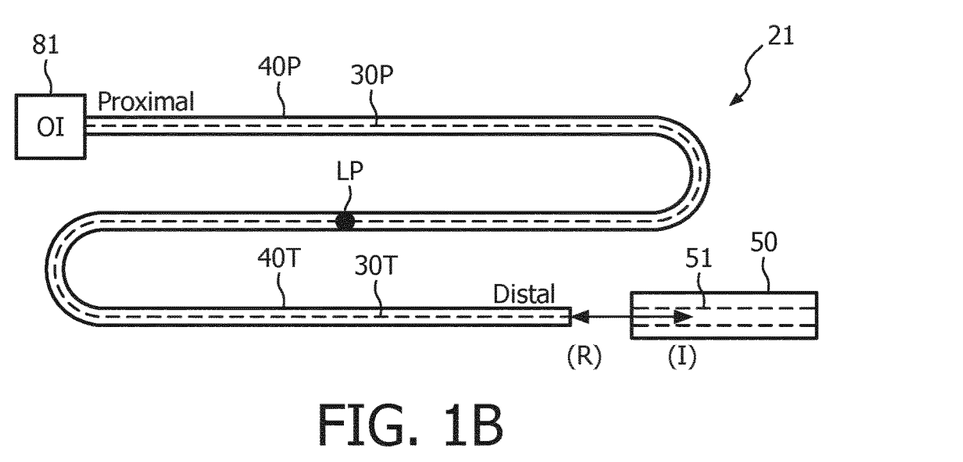
Figure 1C:
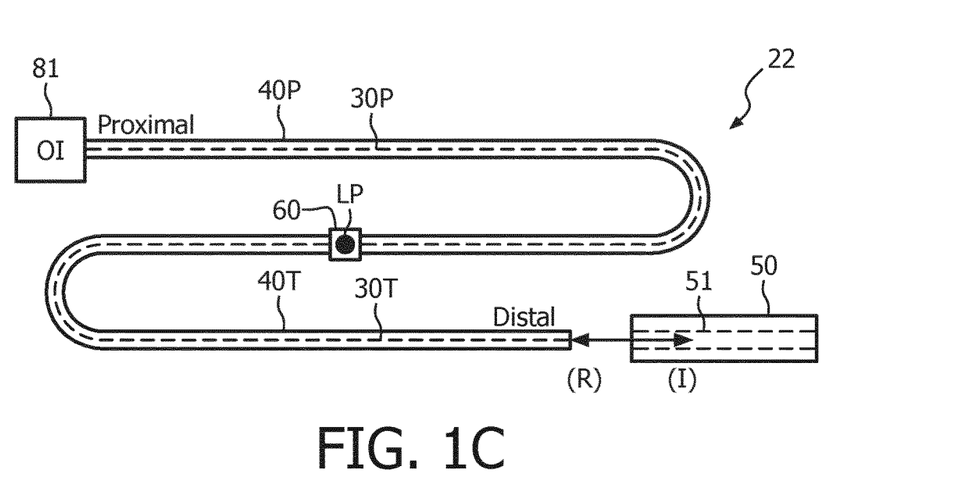

Referring to FIGS. 1A-1C, respective universal FORS inserts 20-22 of the present disclosure employ a FORS sensor 30 in the form of an optical fiber including a proximal segment 30P and a tracking segment 30T having a boundary defined by a launch point LP corresponding to or distally spaced from a most proximal sensing point of controlled grating patterns within the optical fiber (e.g., Fiber Bragg Gratings), a characteristic backscatter of the optical fiber (e.g., Rayleigh backscatter) or any other arrangement of reflective elements and/or transmissive elements embedded, etched, imprinted, or otherwise formed in the optical fiber. In practice, the controlled gratings, characteristic backscatter, or reflective/transmissive elements may extend along any portion and an entirety of the optical fiber.

For universal FORS inserts 20-22 as respectively shown in FIGS. 1A-1C, launch point LP is approximately mid-point between a proximal end and a distal end of universal FORS inserts 20-22 whereby proximal segment 30P extends between the proximal end of universal FORS inserts 20-22 and launch point LP, and tracking segment 30T extends between launch point LP and a distal end of universal FORS inserts 20-22.

Figure 11:
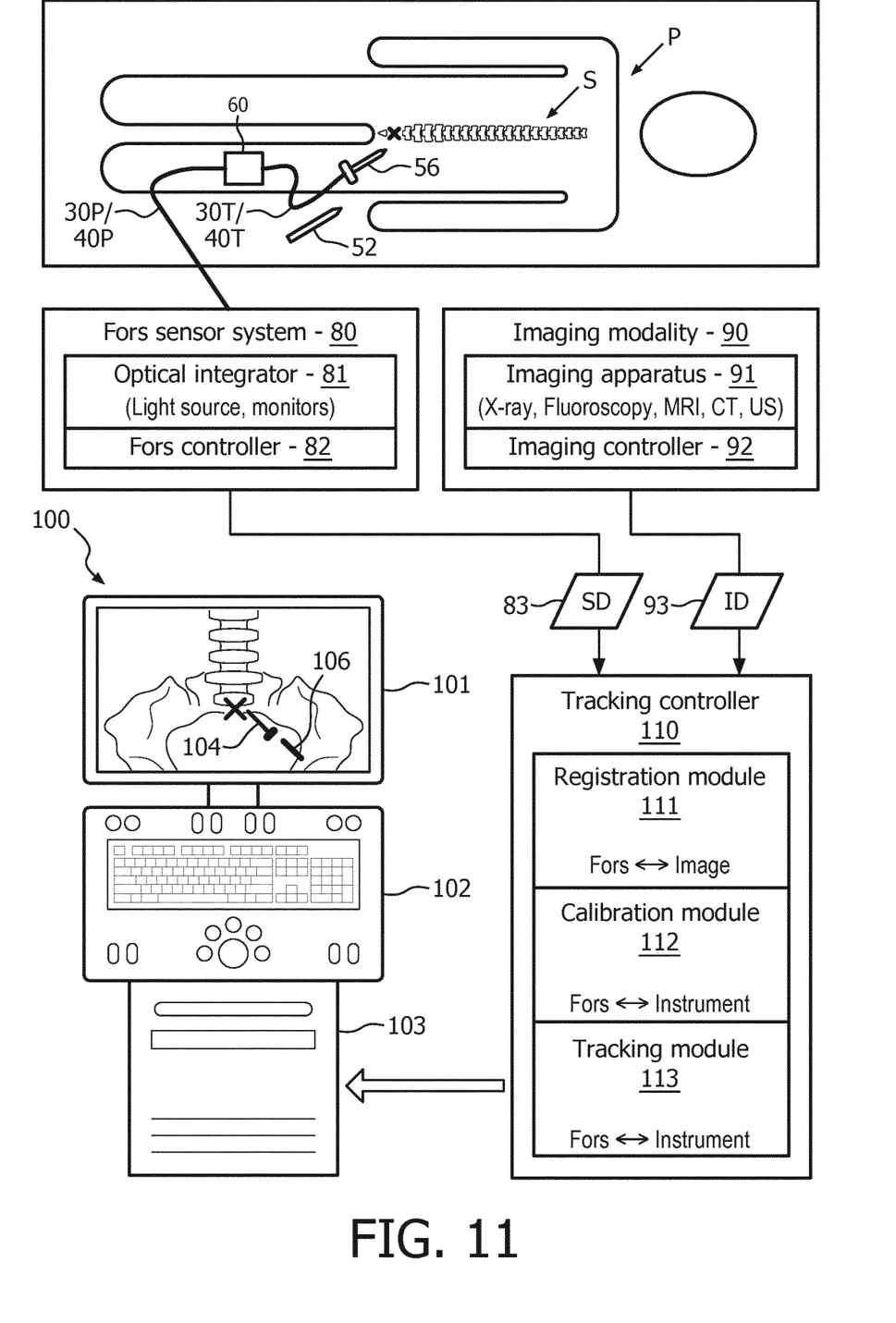
FIG. 11 illustrates an exemplary embodiment of a universal orthopedic tracking system in accordance with the inventive principles of the present invention.

Universal FORS insert 22 as shown in FIG. 1C further employs a launch 60 adjoined to universal FORS insert 22 at launch point LP as will be further described herein in connection with FIG. 11.

In practice, the FORS sensor 30 may be made partially or entirely of any glass, silica, phosphate glass or other glasses, or made of glass and plastic or plastic, or other materials used for making optical fibers. For impeding any damage to FORS sensor 30, universal FORS inserts 20-22 therefore further employ a protective sleeve permanently encircling FORS sensor 30. In practice, protective sleeve 40 may be made from any flexible material of a specified hardness including, but not limited to, pebax, nitinol, furcation tubing, and stranded metal tubing. Also in practice, protective sleeve may consist of two or more tubular components of sane or different degrees of flexibility and hardness in an overlapping and/or sequential arrangement.

For universal FORS insert 20 as shown in FIG. 1A, a protective sleeve 40 permanently encircles an entirety of FORS sensor 30 from the proximal end to the distal end.

For universal FORS inserts 21 and 22 as respectively shown in FIGS. 1B and 1C, a protective sleeve 40 includes a proximal protective sleeve component 40P permanently encircling proximal segment 30P of FORS sensor 30 from the proximal end of FORS sensor 30 to launch point LP, and a tracking protective sleeve component 40T permanently encircling tracking segment 30T of FORS sensor 30 from launch point LP to the distal end for FORS sensor 30.

Referring still to FIGS. 1A-1C, proximal segment 30T as permanently encircled by protective sleeve 40P is connectable to an optical integrator 81 as known in the art for emitting a light into FORS sensor 30 at the proximal end of universal FORS inserts 20-22 whereby the light is propagated through the FORS sensor 30 to the distal end thereof. In practice, the distal ends of universal FORS inserts 20-22 may be closed, particularly for light reflective embodiments of FORS sensor 30, or may be opened, particularly for light transmissive embodiments of FORS sensor 30.

Tracking segment 30T and protective sleeve 40/40T have diameters sized to be insertable (I) into and retractable (R) from within a lumen of a plurality of surgical instruments, such as, for example, a lumen 51 of a surgical instrument 50 representative of surgical instruments being a same version of a same instrument type of surgical instrument or a different version of a same instrument type of surgical instrument, or different instrument types of surgical instruments.

In practice, upon insertion into the lumen of the surgical instrument, tracking segment 30T as permanently encircled by protective sleeve 40/40T may partially or entirely occupy the space of the lumen of the surgical instrument, or extend through and out of the lumen of the surgical instrument, depending on the intended tracking use of universal FORS inserts 20-22.

Figure 2A:
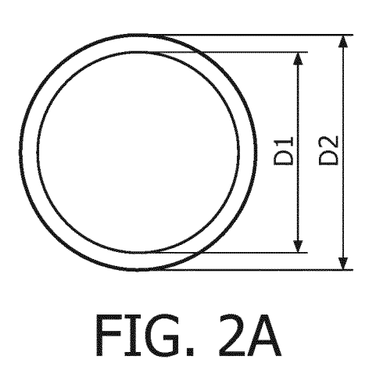
FIGS. 2A and 2B illustrates exemplary relative diameters of a FORS sensor and a protective sleeve in accordance with the inventive principles of the present disclosure.
Figure 2B:
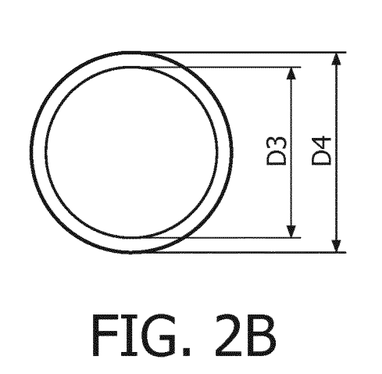

In practice, diameters of proximal segment 30P and tracking segment 30T of the optical fiber may be equal. For example, FIG. 2A illustrates a diameter D1 for proximal segment 30P and tracking segment 30T, and a diameter D2 for protective sleeve 40/40P/40T. Also in practice, a diameter of tracking segment 30T may be less than or greater than a diameter of proximal segment 30P, particularly adjacent a distal end of the universal FORS insert. For example, FIG. 2B illustrates a diameter D3 for tracking segment 30T, which is less than diameter D1 for proximal segment 30P as shown in FIG. 2A, and a diameter D4 for protective sleeve 40/40T permanently encircling tracking segment 30T, which is less than diameter D2 for protective sleeve 40/40P permanently encircling proximal segment 30P.

Figure 3:
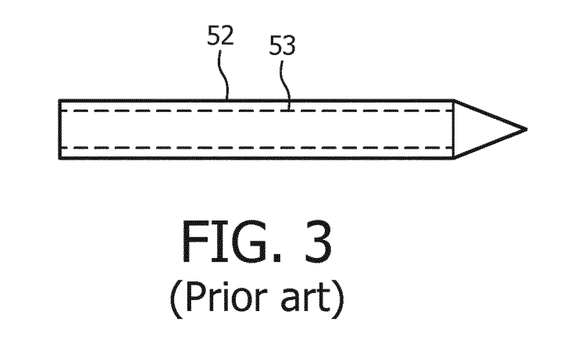
FIG. 3 illustrates an exemplary embodiment of a K-wire as known in the art.
Figure 4:
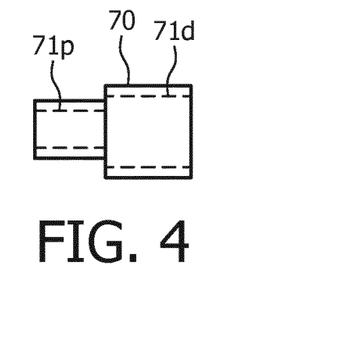
FIG. 4 illustrates an exemplary embodiment of a universal insert receiver in the form of a connector in accordance with the inventive principles of the present disclosure.

In practice, a surgical instrument may be constructed with a lumen as known in the art. For example, FIG. 3 illustrates a k-wire 52 having a lumen 53 construed therein. For such surgical instruments, tracking segment 30T as permanently encircled by protective sleeve 40 may be friction fitted within the lumen upon insertion therein, and/or a universal insert receiver of the present disclosure having a lumen for receiving a universal FORS insert of the present disclosure to thereby affix the universal FORS insert to the surgical instrument in a manner that aligns a lumen of the universal insert receiver with the lumen of the surgical instrument. For example, FIG. 4 illustrates a universal insert receiver in the form of a universal insert connector 70 having a lumen with a proximal band 71p and a distal band 71d, whereby tracking segment 30T as permanently encircled by protective sleeve 40 may be extended through both bands 71a and 71b and friction fitted with proximal band 71a, and a proximal end of a lumen of a surgical instrument may be friction fitted within distal band 71d as will further be explained with the description of FIG. 6B.

For surgical instruments that are typically not constructed with a lumen or do not have an additional lumen available for a universal FORS insert of the present disclosure, a universal insert receiver having a lumen for receiving a universal FORS insert of the present disclosure may be integrated into the surgical instruments (e.g., the connector may be manufactured as a component of the surgical instrument or permanently affixed to the surgical instrument) or retrofitted onto the surgical instrument (e.g., via a detachable press fit or magnetic clamping onto a suitable component of the surgical instrument).

Figure 5A:
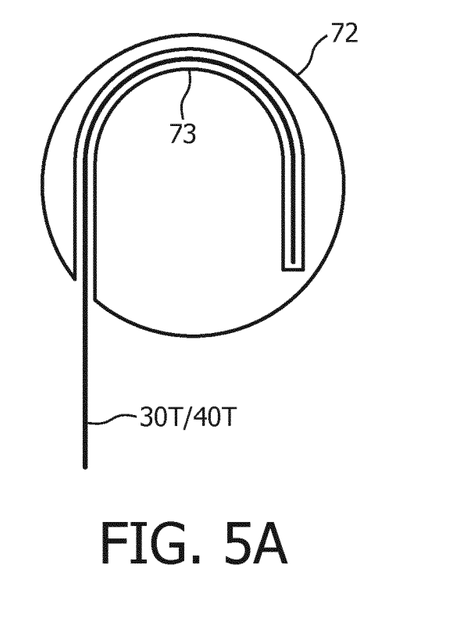
FIGS. 5A and 5B illustrate exemplary embodiments of a universal insert receiver in the form of universal insert clips in accordance with the inventive principles of the present disclosure.
Figure 5B:
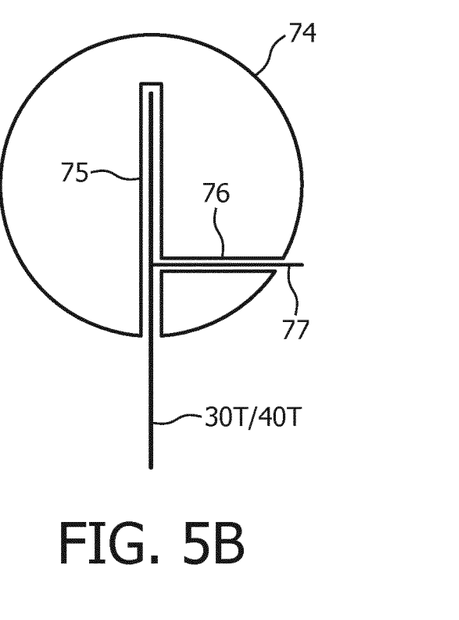

For example, FIG. 5A illustrates a universal insert receiver in the form of a universal insert clip 72 having a lumen 73 of a semi-oval shape for a friction fitted insertion and retraction of a tracking segment as permanently encircled by a protective sleeve (e.g., tracking segment 30T as permanently encircled by a protective sleeve 40T as shown). Also by example, FIG. 5B illustrates a universal insert receiver in the form of a universal insert clip 74 having a lumen 75 for insertion and retraction of a tracking segment as permanently encircled by a protective sleeve (e.g., tracking segment 30T as permanently encircled by a protective sleeve 40T as shown), and a screw 77 extending through a channel 76 intersecting lumen 75 for securing the universal FORS insert as inserted within lumen 75. For both examples, clips 72 and 74 may be integrated into or retrofitted onto a surgical instrument.

To further facilitate an understanding of the various inventions of the present disclosure, the following is a descriptions of universal FORS insert 22 (FIG. 1C) inserted within various orthopedic instruments as shown in FIGS. 6A-10B. Please note the components of the universal FORS insert 22 and the orthopedic instruments as shown in FIGS. 6A-10B are not drawn to scale, but drawn to conceptually visualize the inventive principles of the present disclosure.

Figure 6A:
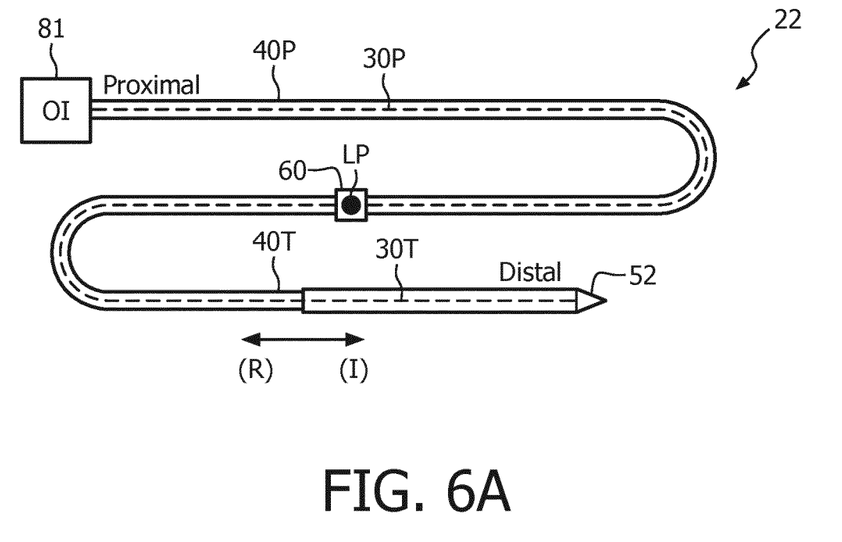
FIGS. 6A and 6B illustrate exemplary insertions of a universal FORS insert into a lumen of a k-wire in accordance with the inventive principles of the present disclosure.
Figure 6B:
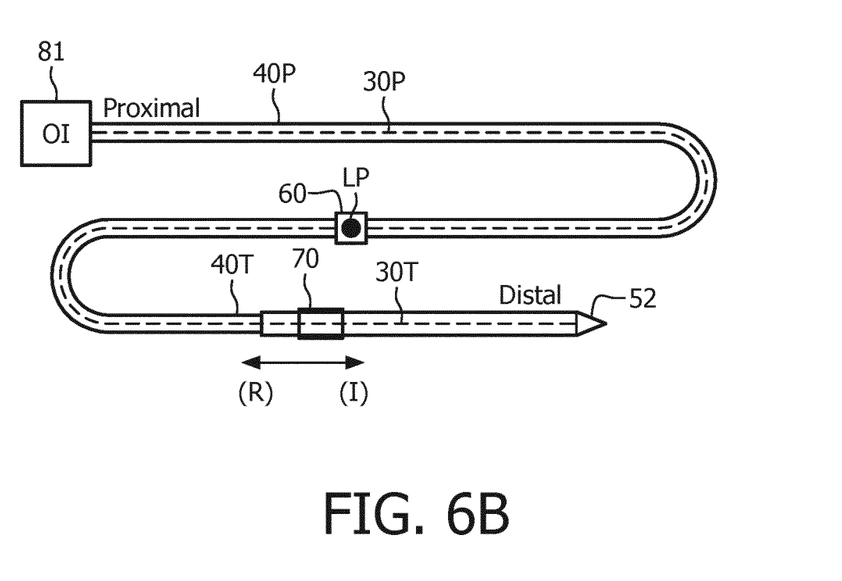

FIG. 6A illustrates tracking segment 30T as permanently encircled by protective sleeve 40T inserted and friction fitted within a lumen 53 (FIG. 3) of k-wire 52. FIG. 6B illustrates tracking segment 30T as permanently encircled by protective sleeve 40T frictionally fitted within and extending through bands 71 (FIG. 4) of universal insert connector 70 into lumen 53 of k-wire 52 with a proximal end of k-wire 52 being friction fitted within distal band 71d (FIG. 4) of universal insert connector 70.

Alternatively in practice, when a k-wire is very thin and thus may not have a mechanical integrity for a lumen, a universal insert clip (e.g., clips 72 and 74 as shown in FIGS. 5A and 5B) may be press-fitted/mechanically clamped onto the k-wire in a manner that aligns the distal end of the universal FORS insert adjacent a proximal end of k-wire 51, and protective sleeve 40 may be optimally designed to an appropriate degree of flexibility whereby tracking segment 30T matches the mechanical movements of the k-wire.

From FIGS. 6A and 6B, those having ordinary skill in the art will appreciate the reusability of a universal FORS insert of the present disclosure for numerous and various sized k-wires as well as similar surgical instruments. In particular, a retraction of tracking segment 30T and protective sleeve 40 from within lumen 53 of k-wire 52 as shown in FIGS. 6A and 6B enables an insertion of tracking segment 30T as permanently encircled by protective sleeve 40T into a lumen of another k-wire of a same size of a different size. More particularly if a clip is utilized, the universal insert clip is unfitted/unclamped from the k-wire and press-fitted/mechanically clamped onto another k-wire of a same size or a different size. Alternatively, tracking segment 30T as permanently encircled by protective sleeve 40T may be retracted from within lumen 53 of the k-wire 52 and then inserted into a lumen of a universal insert clip that is then press-fitted/mechanically clamped onto a different instrument.

Figure 7A:
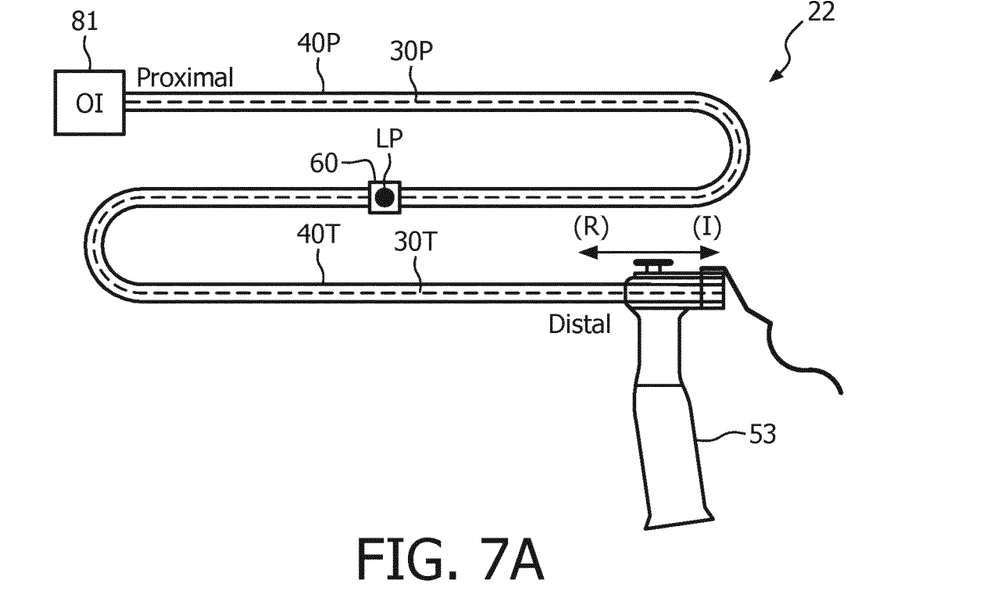
FIGS. 7A and 7B illustrate exemplary insertions of a universal FORS insert into a lumen of a k-wire driver in accordance with the inventive principles of the present disclosure.
Figure 7B:
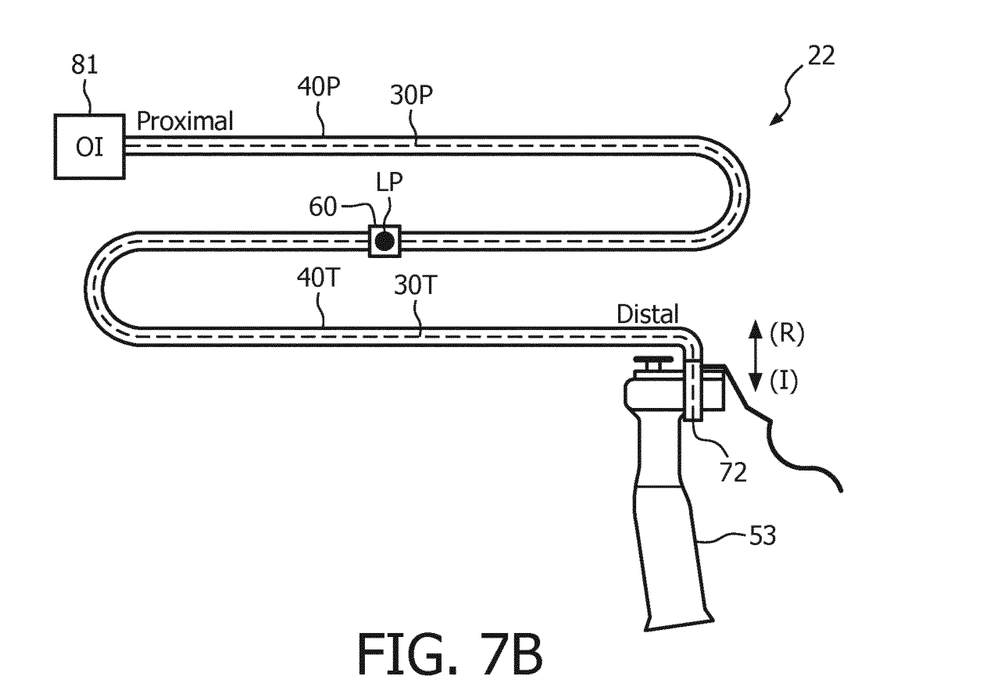

FIG. 7A illustrates tracking segment 30T as permanently encircled by protective sleeve 40T inserted and friction fitted within a lumen of a k-wire driver 53. FIG. 7B illustrates tracking segment 30T as permanently encircled by protective sleeve 40T inserted and friction fitted within a lumen 73 (FIG. 5A) of universal insert clip 72 press-fitted/mechanically clamped onto k-wire driver 53. From FIGS. 7A and 7B, those having ordinary skill in the art will appreciate the reusability of universal FORS inserts of the present disclosure for numerous and various types of k-wire drivers as well as similar surgical instruments. In particular, a retraction of tracking segment 30T as permanently encircled by protective sleeve 40T from within the lumen of k-wire driver 53 as shown in FIG. 7A enables an insertion of tracking segment 30T as permanently encircled by protective sleeve 40T into a lumen of another k-wire driver of a same version or a different version. More particularly, universal inset clip 72 as shown in FIG. 7B may be unfitted/unclamped from k-wire driver 53 and press-fitted/mechanically clamped onto another k-wire driver of the same version or a different version.

Figure 8A:
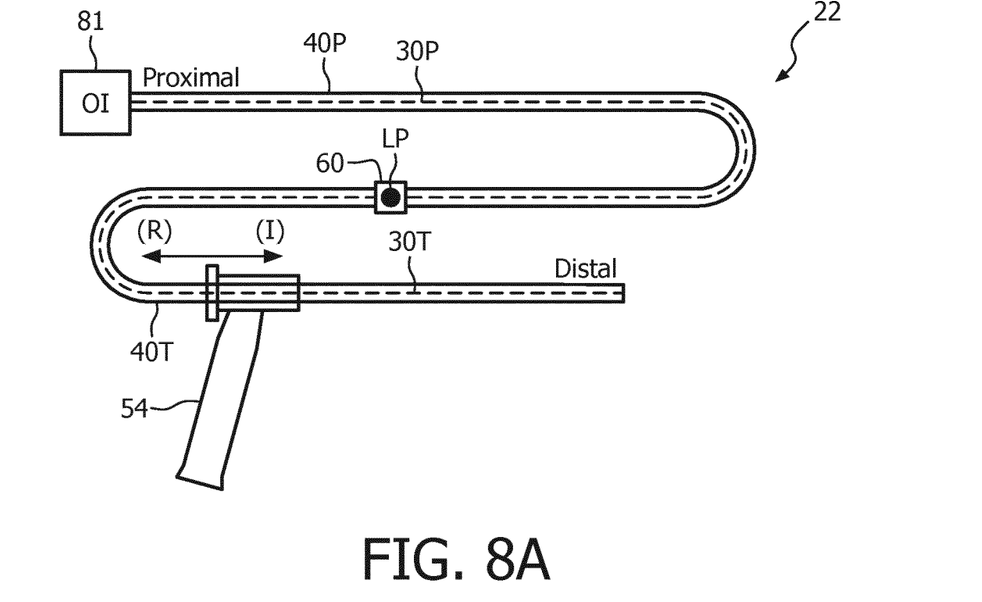
FIGS. 8A and 8B illustrate exemplary insertions of a universal FORS insert into a lumen of an endoscope in accordance with the inventive principles of the present disclosure.
Figure 8B:
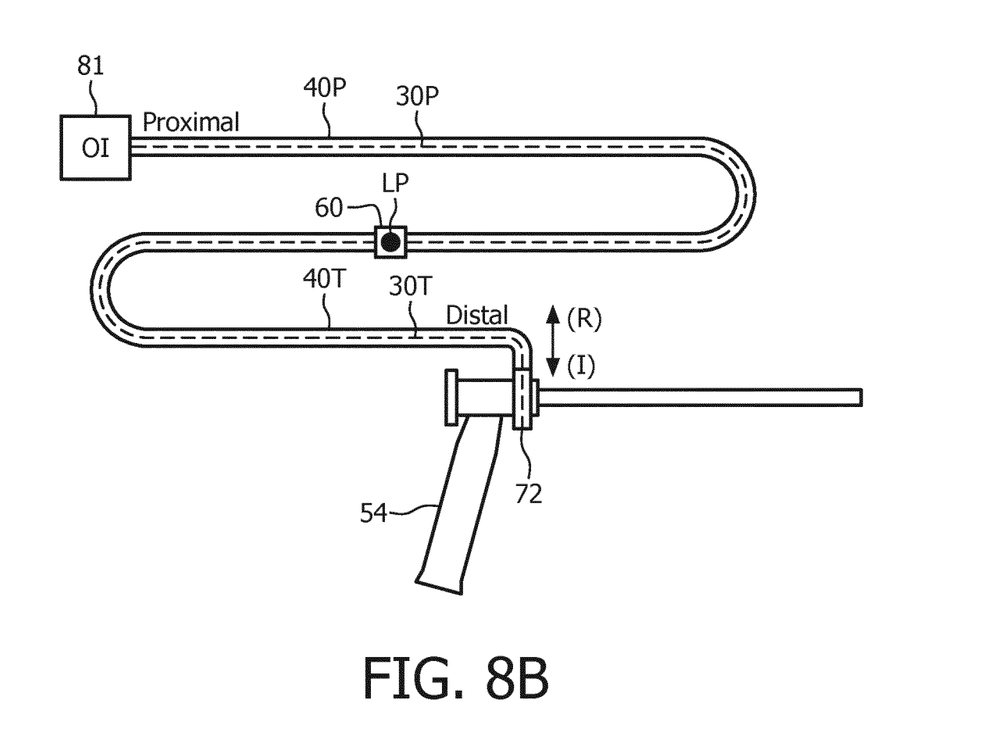

FIG. 8A illustrates tracking segment 30T as permanently encircled by protective sleeve 40T inserted and friction fitted within a lumen of an endoscope 54. FIG. 8B illustrates tracking segment 30T as permanently encircled by protective sleeve 40T inserted and friction fitted within a lumen 73 (FIG. 5A) of universal insert clip 72 press-fitted/mechanically clamped onto endoscope 54. From FIGS. 8A and 8B, those having ordinary skill in the art will appreciate the reusability of universal FORS inserts of the present disclosure for numerous and various types of endoscopes as well as similar surgical instruments. In particular, a retraction of tracking segment 30T as permanently encircled by protective sleeve 40T from within the lumen of endoscope 54 as shown in FIG. 8A enables an insertion of tracking segment 30T as permanently encircled by protective sleeve 40T into a lumen of another endoscope of a same version or a different version. More particularly, clip 72 as shown in FIG. 8B may be unfitted/unclamped from endoscope 54 and press-fitted/mechanically clamped onto another endoscope of the same version or a different version.

Figure 9A:
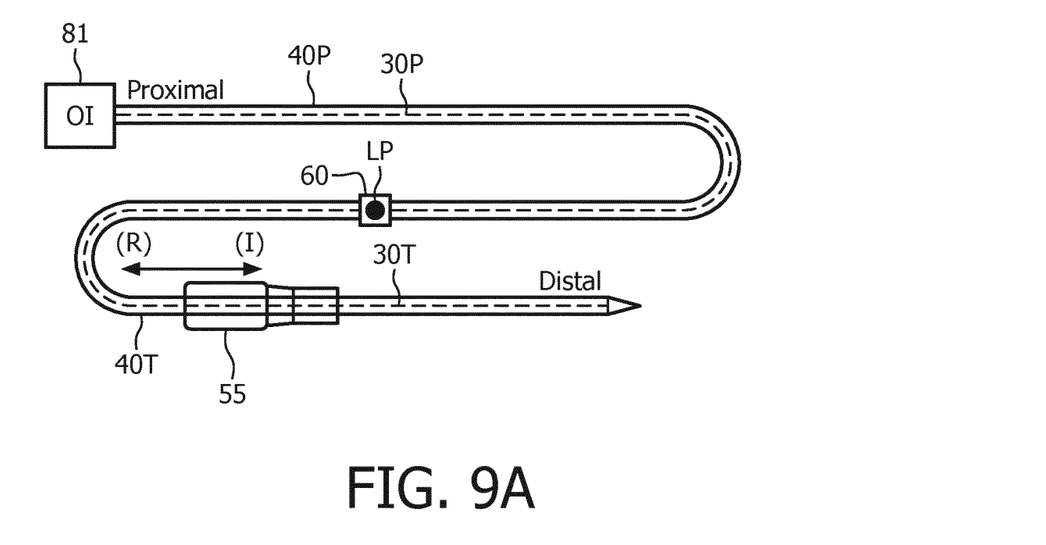
FIGS. 9A and 9B illustrate exemplary insertions of a universal FORS insert into a lumen of an awl in accordance with the inventive principles of the present disclosure.
Figure 9B:
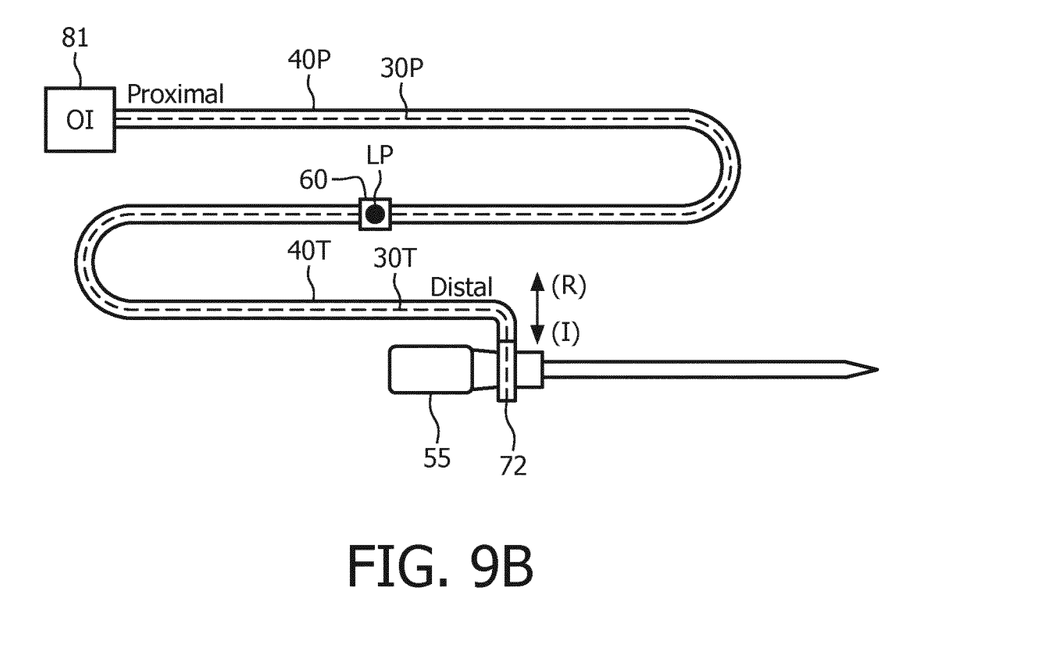

FIG. 9A illustrates tracking segment 30T as permanently encircled by protective sleeve 40T inserted and friction fitted within a lumen of an awl 55. FIG. 9B illustrates tracking segment 30T as permanently encircled by protective sleeve 40T inserted and friction fitted within a lumen 73 (FIG. 5A) of universal insert clip 72 press-fitted/mechanically clamped onto awl 55. From FIGS. 9A and 9B, those having ordinary skill in the art will appreciate the reusability of universal FORS inserts of the present disclosure for numerous and various types of awls as well as similar surgical instruments. In particular, a retraction of tracking segment 30T as permanently encircled by protective sleeve 40T from within the lumen of awl 55 as shown in FIG. 9A enables an insertion of tracking segment 30T as permanently encircled by protective sleeve 40T into a lumen of another awl of a same version or a different version. More particularly, clip 72 as shown in FIG. 9B may be unfitted/unclamped from awl 55 and press-fitted/mechanically clamped onto another awl of the same version or a different version.

Figure 10A:
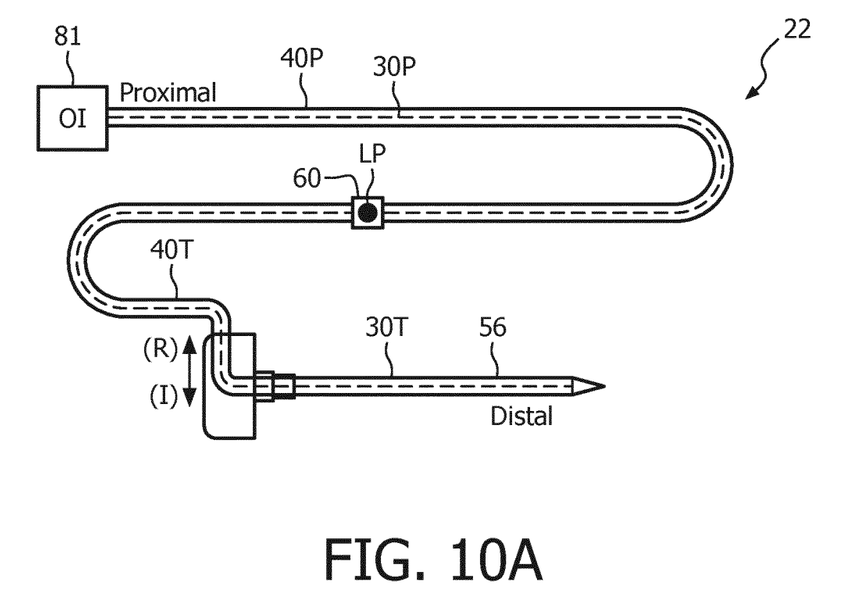
FIGS. 10A and 10B illustrate exemplary insertions of a universal FORS insert into a lumen of a j-needle in accordance with the inventive principles of the present disclosure.
Figure 10B:
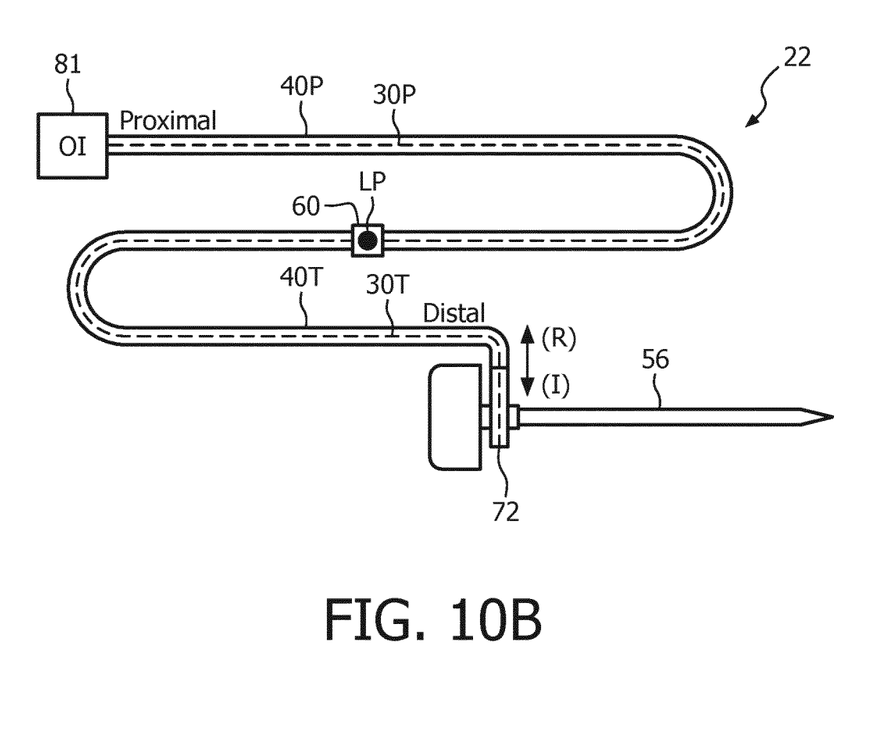

FIG. 10A illustrates tracking segment 30T as permanently encircled by protective sleeve 40T inserted and friction fitted within a lumen of a j-needle 56. FIG. 10B illustrates tracking segment 30T as permanently encircled by protective sleeve 40T inserted and friction fitted within a lumen 73 (FIG. 5A) of universal inset clip 72 press-fitted/mechanically clamped onto j-needle 56. From FIGS. 10A and 10B, those having ordinary skill in the art will appreciate the reusability of universal FORS inserts of the present disclosure for numerous and various types of j-needles and similar surgical instruments. In particular, a retraction of tracking segment 30T as permanently encircled by protective sleeve 40T from within the lumen of j-needle 56 as shown in FIG. 10A enables an insertion of tracking segment 30T as permanently encircled by protective sleeve 40T into a lumen of another j-needle of a same version or a different version. More particularly, clip 72 as shown in FIG. 10B may be unfitted/unclamped from j-needle 56 and press-fitted/mechanically clamped onto another j-needle of the same version or a different version.

To facilitate an understanding of universal FORS tracking systems of the present disclosure, the following description of a universal FORS tracking system as shown in FIG. 11 is directed a universal FORS insert 22 (FIG. 1) tracking k-wire 52 (FIG. 3) and j-needle 56 (FIGS. 10A-10B) during a surgical procedure of a spine S for a patient P. From the description of FIGS. 11-13, those having ordinary skill in the art will appreciate how to apply the inventive principles of the present disclosure for tracking numerous and various types of surgical procedures.

Referring to FIG. 11, the universal FORS tracking system of the present disclosure employs a FORS system 80, an imaging modality 90, a workstation 100 and a tracking controller 110 installed on workstation 100.

In one embodiment as known in the art, FORS sensor system 80 includes optical integrator 81 (FIG. 1) and a FORS controller 82 directing a broadband optical source of optical integrator 81 for emitting a light into proximal segment 30T as permanently encircled by launch protective sleeve 40T whereby a reflection wavelength monitor of optical integrator 81 monitors all reflection of the propagated light back by tracking segment 30T to the proximal end of universal FORS insert 22 and/or a transmission wavelength monitor of optical integrator 81 monitors all transmission of the propagated light by tracking segment 30T via the distal end of universal FORS insert 22. From the reflected and/or transmitted light, FORS controller 82 controls a communication to tracking controller 110 of sensor data ("SD") 83 indicative of a reconstructed shape of tracking segment 30T within a frame coordinate system referenced by launch 60.

In practice, launch 60 may be fixed to a point in the room, such as, for example, a surgical rail of an operating table as shown or a patient P.

Imaging modality 90 is one of a known imaging modalities including, but not limited to, X-ray, fluoroscopy, CT, MRI and ultrasound. Imaging modality 90 includes an imaging apparatus 91 for generating imaging data ("ID") 93 of a spine S of patient, and an imaging controller 92 to control a communication of imaging data 93 to tracking controller 110.

Workstation 100 includes a known arrangement of a monitor 101, a keyboard 101 and a computer 103.

Tracking controller 110 includes application modules in the form of a registration module 111 for registering universal FORS insert 22 to imaging modality 90, a calibration module 112 for calibrating an universal FORS insert 22 to j-needle 56 and k-wire 52, and a tracking module 113 for display a tracking visualization of j-needle 56 and k-wire 52 within the image of spine S of patient P registered to universal FORS insert 22.

An exemplary workflow of the universal FORS tracking system including a registration phase, a calibration phase and a tracking phase will now be described herein. The X on patient P represents an incision point of patient P.

Registration Phase. A user of the system sets up FORS sensor system 80 via various coupling of universal FORS insert 22 to the broadband optical source and wavelength monitors via a circulator as known in the art, and positions launcher 60 relative to patient P (e.g., attached to a rail of the bed of patient P). The user subsequently activates registration module 91 via keyboard 102 as needed to register a launch position of FORS sensor 22 or another registration position of FORS sensor 22 distally spaced from the launch position to a pre-operative image or an intra-operative image of spine S of patient P generated by imaging modality 90 as represented by imaging data 93. In practice, any known applicable registration technique may be executed by registration module 111 for registering universal FORS insert 22 to the image of the spine S of patient P.

Calibration Phase. The user of the system securely adjoins universal FORS insert 22 to a surgical instrument (e.g., inserts a tracking segment of universal FORS insert 22 within a lumen of the surgical instrument as previously described herein). The user subsequently activates calibration module 112 via keyboard 112 as needed to calibrate universal FORS insert 22 to the surgical instrument.

More particularly for a universal insert clip (e.g., universal insert clips 72 and 74 respectively shown in FIGS. 5A and 5B), the calibration is premised on a rigid relationship between the surgical instrument and the universal inset clip. As such, in practice, any known applicable calibration technique may be executed for calibrating universal FORS insert 22 and the surgical instrument including, but not limited to:

(1) an implementation of a calibration database for all surgical instruments and repeatable universal attachments;

(2) a real-time calibration by leaving the surgical instrument stationary and touching the distal end of the surgical instrument with distal end of universal FORS insert 22 before sliding the distal end of universal FORS insert 21 into the universal insert clip;

(3) X-ray (or other image-based) registration (in this case, the registration and calibration phases are combined); and (4) real-time calibration using methods known in the art, such as pivoting the distal end of the surgical instrument with universal FORS insert 22 attached thereof around a fixed reference point.

Alternative to known calibration techniques, the present disclosure provides a calibration technique involving an automatic detection and calibration of a given surgical instrument through a lumen shape that is unique to each surgical instrument or to a universal insert receiver of the present disclosure. Specifically, once the universal FORS insert of the present disclosure is passed into the lumen of the surgical instrument or the lumen of an universal insert receiver, calibration module 112 automatically detects which surgical instrument or universal insert receiver is being used based on one or more of shape parameters (curvature, position, orientation, axial strain, etc.) of the reconstructed shape of the tracking segment of the FORS sensor.

For example, by virtue of the shape parameters of the lumen of k-wire 52 as shown in FIG. 6A, calibration module 112 would recognize a reconstructed shape of tracking segment 30T as inserted into the lumen of k-wire 52, and then automatically load the calibration information for that particular version of k-wire 52. Conversely, by virtue of the curvature of the lumen of j-needle 56 as shown in FIG. 10A, calibration module 112 would recognize a reconstructed shape of tracking segment 30T as inserted into the lumen of j-needle 56, and then automatically load the calibration information for that particular version of j-needle 56.

Figure 13:
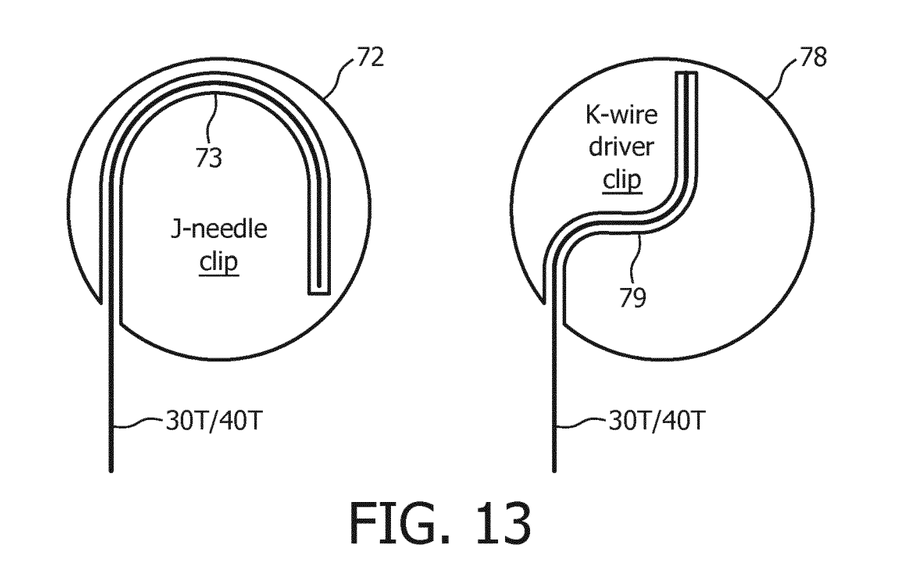
FIG. 13 illustrates exemplary embodiments of a universal insert receiver in the form of identifiable universal insert clips in accordance with the inventive principles of the present disclosure.

By further example, FIG. 13 illustrates a universal insert clip 72 having a lumen 73 of a specific unique curvature that is adjoinable to a j-needle, and a universal insert clip 78 having a lumen 79 of a specific unique curvature distinct from the curvature of lumen 73 that is adjoinable to a k-wire driver. By virtue of the curvature of lumen 73, calibration module 112 would recognize the reconstructed shape of tracking segment 30T as inserted into lumen 73, and then automatically load the calibration information for that particular version of j-needle. Conversely, by virtue of the curvature of lumen 79, calibration module 112 would recognize the reconstructed shape of tracking segment 30T as inserted into lumen 79, and then automatically load the calibration information for that particular version of k-wire driver.

Tracking Phase. Upon completion of registration and calibration, tracking module 113 controls a visualization of an overlay of the surgical instrument on the pre-operative image or the intra-operative image as shown on monitor 101 based on the shape sensing position indicated by sensing data 83 registered to imaging data 93.

In practice, a working surgical instrument can be selected from a database, and then a model of the surgical instrument will be displayed based on the shape sensing position of universal FORS insert 22. The model can simply be a thicker diameter line for the surgical instrument, or an actual model of the surgical instrument attached to the end of a screw driver (not shown).

Also in practice, a tracking accuracy may be refined as desired.

For example, an image-based refinement may involve the user of the system identifying a tip of the surgical instrument in the image overlay whereby a distance between the distal ends of universal FORS insert 22 and the surgical instrument is measured and then used to extrapolate the shape of universal FORS insert 22 by the appropriate amount. If there is significant error that is not in the longitudinal direction of the surgical instrument, then this error is detected and identified to the user.

By further example, in pre-calibration, the user may place the tip of universal FORS insert 22 into a specific position on launch 60 (or another known position), and a distance between the known position and the measured position of the distal end of universal FORS insert 22 is computed. If there is significant error that is not in the longitudinal direction of the distal end of universal FORS insert 22, then this error is detected and identified to the user.

By further example, an execution of a known technique for determining longitudinal offset between a tip of universal FORS insert 22 and measurement of the tip of the universal FORS insert 22 is implemented by the user through a pivot fixture.

Still referring to FIG. 11, in practice, navigation by the system may be implemented manually or robotically. Furthermore, while tracking controller 110 is shown independent of FORS controller 82 and imaging controller 92, in practice tracking controller 110 may be integrated with FORS controller 82 and/or imaging controller 92 within the same workstation (e.g., workstation 100), and/or may be independently installed on the same platform as FORS controller 82 and/or imaging controller 92 (e.g., workstation 100).

Upon completion of the workflow phases for the surgical instrument, universal FORS insert 22 may be retracted from the lumen of the surgical instrument whereby universal FORS insert 22 may be inserted into a lumen of another surgical instrument of the same instrument type or different type for the same or different surgical procedure.

Figure 12:
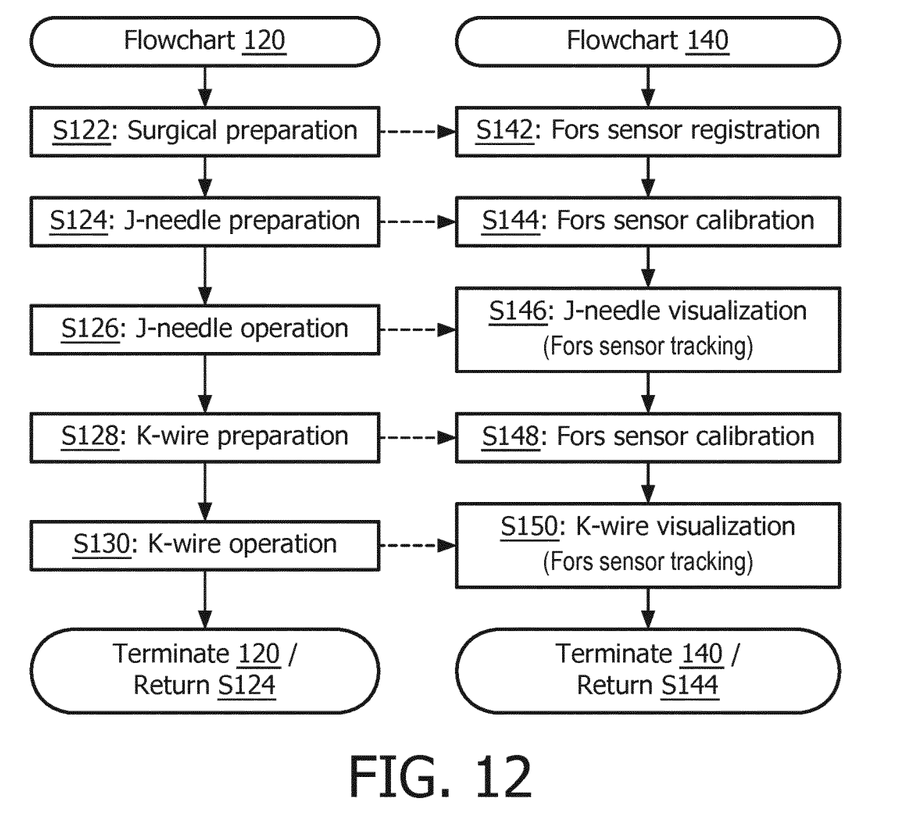
FIG. 12 illustrates flowcharts representative of an exemplary orthopedic procedure in accordance with the inventive principles of the present invention.

FIG. 12 illustrates flowcharts 120 and 140 as an application of the aforementioned workflow in the context of an orthopedic procedure involving k-wire 52 and j-needle 56 as shown in FIG. 11. Flowchart 120 represents actions performed by a surgical team during the orthopedic procedure and, and flowchart 140 represents actions executed by workstation 100 as shown in FIG. 11 as directed by the surgical team.

Referring to FIGS. 11 and 12, a stage S122 of flowchart 120 involves the surgical team preparing for the surgery by (1) positioning patient P prone on the operating table,
(2) positioning a C-arm to acquire a good view of a pedicle of patient P, and
(3) performing necessary actions for registering FORS sensor 30 to image modality 90 as previously described herein.

Stage S122 further involves a surgical team member interfacing with registration module 111 dependent upon the particular registration technique to be executed by registration module 111 during a stage S142 of flowchart 140 for the registration of FORS sensor 30 to imaging modality 90.

Upon completion of the surgical preparation, a stage S124 of flowchart 120 involves the surgical team prepping j-needle 56 by (1) press-fitting/magnetically clamping a clip 72 onto j-needle 56 and securely inserting universal FORS insert 22 into a lumen of clip 72 as shown in FIG. 10B, and
(2) performing necessary actions for calibrating FORS sensor 30 to j-needle 56 as previously described herein.

Stage S124 further involves a surgical team member interfacing with calibration module 112 dependent upon the particular calibration technique to be executed by calibration module 112 during a stage S144 of flowchart 140 for the calibration of FORS sensor 30 to j-needle 56.

Upon completion of the j-needle preparation, a stage S126 of flowchart 120 involves the surgical team (1) initiating a tracking of FORS sensor 30 by tracking module 113 during a stage S146 of flowchart 140,
(2) creating access to spine S of patient P,
(3) docking j-needle 56 on the junction between the transverse process and the facet complex, and (4) gently tapping j-needle 56 with a mallet to advance j-needle 56 through the pedicle under fluoroscopic visualization via imaging modality 90 supplemented by a visualization of an overlay 104 of j-needle 56 on a X-ray image displayed on monitor 101.

Overlay 104 is generated by tracking module 113 during stage S146 from sensing data 83 indicative of a shape of tracking segment 30T of universal FORS insert 22 as registered to imaging data 93 of patient P.

Upon j-needle 56 reaching one quarter or half the depth of the vertebral body as visualized on monitor 101, a stage S128 of flowchart 120 involves the surgical team (1) retracting universal FORS insert 22 from within the lumen of clip 72,
(2) securely inserting universal FORS insert 22 into a lumen of k-wire 52 as shown in FIG. 6A, and
(3) performing necessary actions for calibrating a previously registered FORS sensor 30 to k-wire 52 as previously described herein.

Stage S128 further involves a surgical team member interfacing with calibration module 112 dependent upon the particular calibration technique to be executed by calibration module 112 during a stage S148 of flowchart 140 for calibrating FORS sensor 30 to k-wire 52.

Upon completion of the k-wire preparation, a stage S130 of flowchart 120 involves the surgical team (1) removing a cutting tip from an operational lumen of j-needle 56 and inserting k-wire 52 into the operational lumen of j-needle 56,
(2) initiating a tracking of FORS sensor 30 by tracking module 113 during a stage S150 of flowchart 140, and
(3) passing k-wire 52 further into the bone under fluoroscopic visualization via imaging modality 90 supplemented by a visualization of an overlay 106 of k-wire 52 on the X-ray image displayed on monitor 101.

Overlay 106 is generated by tracking module 113 during stage S150 from sensing data 83 indicative of a shape of tracking segment 30T of universal FORS insert 22 as registered to imaging data 93 of patient P.

Stage S130 further involves the surgical team (4) removing j-needle 56,
(5) placing cannulated muscle dilators over k-wire 52, and
(6) tapping the pedicle and placing the appropriate cannulated screw.

Upon placement of the cannulated screw, flowcharts 120 and 140 may be terminated or returned to stages S124 and S144 for placement of an additional cannulated screw under the visual guidance of tracking controller 110.

From the preceding description of flowcharts 120 and 140, those having ordinary skill in the art will appreciate the benefit of an application of a universal FORS insert and system of the present disclosure.

More particularly, referring to FIGS. 1-13, those having ordinary skill in the art will appreciate numerous benefits of the present invention including, but not limited to, overcoming the drawbacks of known optical and electromagnetic tracking of surgical instruments during a surgical procedure, particularly known optical and electromagnetic tracking of orthopedic instruments during an orthopedic surgery involving the musculoskeletal system (e.g., spinal fixation, pedicle screw placement, trauma surgery, oncology and neurosurgery).

For example, one key limitation of optical trackers is that the large size of optical trackers precludes their use with many of the orthopedic instruments. The small footprint (e.g., 200 um) provided by a FORS sensor provides unique opportunities to track orthopedic instruments which were previously deemed untrackable (e.g., k-wire and j-needle).

Furthermore, current optical navigation systems only track a single position of the orthopedic instrument. Due to the size of the optical trackers, the optical trackers are typically affixed to a large tool such as a drill handle and then used to make an indirect measurement of the tip of the tool. This may be acceptable for orthopedic instruments that are rigid, but for orthopedic instruments that are <3 mm in diameter, the relationship between the tip of an orthopedic instrument and an optical tracker is not rigid due to the flexibility of the orthopedic instrument. With a FORS sensor adjoined to the orthopedic instrument, any flexing of the orthopedic instrument may be visualized as well as a complete trajectory of the orthopedic instrument through the anatomical structure. Most importantly the tip position of the orthopedic instrument can be accurately known at all times.

Moreover, FORS sensors do not require a line-of-sight required by optical trackers and have a lightweight footprint as compared to optical trackers.

Further, as one having ordinary skill in the art will appreciate in view of the teachings provided herein, features, elements, components, etc. described in the present disclosure/specification and/or depicted in the Figures may be implemented in various combinations of hardware and software, and provide functions which may be combined in a single element or multiple elements. For example, the functions of the various features, elements, components, etc. shown/illustrated/depicted in the Figures can be provided through the use of dedicated hardware as well as hardware capable of executing software in association with appropriate software for added functionality. When provided by a processor, the functions can be provided by a single dedicated processor, by a single shared processor, or by a plurality of individual processors, some of which can be shared and/or multiplexed. Moreover, explicit use of the term "processor" or "controller" should not be construed to refer exclusively to hardware capable of executing software, and can implicitly include, without limitation, digital signal processor ("DSP") hardware, memory (e.g., read only memory ("ROM") for storing software, random access memory ("RAM"), non-volatile storage, etc.) and virtually any means and/or machine (including hardware, software, firmware, combinations thereof, etc.) which is capable of (and/or configurable) to perform and/or control a process.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (e.g., any elements developed that can perform the same or substantially similar function, regardless of structure). Thus, for example, it will be appreciated by one having ordinary skill in the art in view of the teachings provided herein that any block diagrams presented herein can represent conceptual views of illustrative system components and/or circuitry embodying the principles of the invention. Similarly, one having ordinary skill in the art should appreciate in view of the teachings provided herein that any flow charts, flow diagrams and the like can represent various processes which can be substantially represented in computer readable storage media and so executed by a computer, processor or other device with processing capabilities, whether or not such computer or processor is explicitly shown.

Having described preferred and exemplary embodiments of novel and inventive universal Fiber Optical RealShape insert for tracking surgical instruments during a surgical procedure, (which embodiments are intended to be illustrative and not limiting), it is noted that modifications and variations can be made by persons skilled in the art in light of the teachings provided herein, including the Figures. It is therefore to be understood that changes can be made in/to the preferred and exemplary embodiments of the present disclosure which are within the scope of the embodiments disclosed herein.

Moreover, it is contemplated that corresponding and/or related systems incorporating and/or implementing the device/system or such as may be used/implemented in/with a device in accordance with the present disclosure are also contemplated and considered to be within the scope of the present invention. Further, corresponding and/or related method for manufacturing and/or using a device and/or system in accordance with the present disclosure are also contemplated and considered to be within the scope of the present invention.

The invention claimed is:

1. A universal FORS insert for a plurality of different surgical instruments, the universal FORS insert comprising:
   a FORS sensor comprising a tracking segment, wherein the FORS sensor is adapted to generate sensing data indicative of a reconstructed shape of the tracking segment;
   a universal insert receiver adapted to be adjoined to each of the plurality of different surgical instruments, wherein the universal insert receiver comprises a lumen having an open end and a closed end; and
   a protective sleeve encircling at least a portion of the tracking segment of the FORS sensor, wherein the at least a portion of the tracking segment permanently encircled by the protective sleeve is adapted to be inserted into and retracted from the open end of the lumen of the universal insert receiver.

2. The universal FORS insert of claim 1, wherein the at least a portion of the tracking segment encircled by the protective sleeve serves as an additional surgical instrument of the plurality of surgical instruments.

3. The universal FORS insert of claim 1, wherein, upon the least a portion of the tracking segment encircled by the protective sleeve being inserted into the lumen of the universal insert receiver as adjoined to one of the surgical instruments, the FORS sensor is further adapted to identify an instrument type of the one of the surgical instruments responsive to the reconstructed shape of the tracking segment.

4. The universal FORS insert of claim 1, further comprising:
   a launch adjoined to FORS sensor,
      wherein the FORS sensor is adpated to generate the sensing data indicative of the reconstructed shape of the tracking segment relative to the launch.

5. The universal FORS insert of claim 1, wherein the plurality of different surgical instruments comprises at least one of a same version of a same instrument type of surgical instrument and different versions of a same instrument type of surgical instrument.

6. The universal FORS insert of claim 1, wherein the plurality of different surgical instruments comprises at least two different instrument types of surgical instruments.

7. A surgical assembly, comprising:
   a plurality of different surgical instruments, each surgical instrument surgical instrument comprising an universal insert receiver adjoined thereto, and each universal insert receiver comprising a lumen having an open end and closed end;

a universal FORS insert comprising:
- a FORS sensor comprising a tracking segment, the FORS sensor being adapted to generate sensing data indicative of a reconstructed shape of the tracking segment; and
- a protective sleeve permanent encircling at least a portion of the tracking segment of the FORS sensor, wherein the at least a portion of the tracking segment encircled by the protective sleeve is adapted to be inserted into and retracted from the open end of the lumen of each universal insert receiver.

8. The surgical assembly of claim 7, wherein the at least a portion of the tracking segment encircled by the protective sleeve serves as an additional surgical instrument of the plurality of surgical instruments.

9. The surgical assembly of claim 7, wherein, upon the least a portion of the tracking segment encircled by the protective sleeve being inserted into the open end of the lumen of one of the universal insert receiver adjoined to one of the surgical instruments, the FORS sensor is further adapted to identify an instrument type of the one of the surgical instruments responsive to the reconstructed shape of the tracking segment.

10. The surgical assembly of claim 7, further comprising:
a launch adjoined to FORS sensor,
wherein the FORS sensor is adapted to generate the sensing data indicative of the reconstructed shape of the tracking segment relative to the launch.

11. The surgical assembly of claim 7, wherein the plurality of different surgical instruments comprises at least one of a same version of a same instrument type of surgical instrument and different versions of a same instrument type of surgical instrument.

12. The surgical assembly of claim 7, wherein the plurality of different surgical instruments comprises at least two different instrument types of surgical instruments.

13. The surgical assembly of claim 7,
wherein a first surgical instrument of the plurality of surgical instruments comprises a universal insert receiver retrofitted onto the first surgical instrument.

14. The surgical assembly of claim 7,
wherein a first surgical instrument of the plurality of surgical instruments comprises a universal insert receiver integrated into the first surgical instrument.

15. The surgical assembly of claim 7,
wherein a first surgical instrument of the plurality of surgical instruments comprises a universal insert receiver detachably attached to the first surgical instrument.

\* \* \* \* \*